(12) United States Patent
Visweswara et al.

(10) Patent No.: US 9,773,395 B2
(45) Date of Patent: Sep. 26, 2017

(54) DEVICE FOR CONVERTING A MOVEMENT OF A USER INTO A VOLTAGE

(71) Applicant: KONINKLIJKE PHILIPS N.V., Eindhoven (NL)

(72) Inventors: Ashoka Sathanur Visweswara, Eindhoven (NL); Wilhelmus Andreas Marinus Arnoldus Maria Van Den Dungen, Boxtel, NC (US); Heribert Baldus, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/029,478

(22) PCT Filed: Oct. 2, 2014

(86) PCT No.: PCT/EP2014/071153
§ 371 (c)(1),
(2) Date: Apr. 14, 2016

(87) PCT Pub. No.: WO2015/055439
PCT Pub. Date: Apr. 23, 2015

(65) Prior Publication Data
US 2016/0275771 A1  Sep. 22, 2016

(30) Foreign Application Priority Data
Oct. 16, 2013  (EP) .................................... 13188799

(51) Int. Cl.
*G08B 23/00* (2006.01)
*G08B 21/04* (2006.01)
(Continued)

(52) U.S. Cl.
CPC .......... *G08B 21/043* (2013.01); *A61B 5/1117* (2013.01); *A61B 5/6822* (2013.01);
(Continued)

(58) Field of Classification Search
CPC .................................................... G08B 21/043
(Continued)

(56) References Cited

U.S. PATENT DOCUMENTS 6,063,036 A * 5/2000 Li ........................ A61B 5/6822
                                                        600/500
2004/0078662 A1  4/2004 Hamel et al.
(Continued)

FOREIGN PATENT DOCUMENTS

| EP | 2549228 A1 | 1/2013 |
| JP | 2002140776 A | 5/2002 |
| WO | 2009138941 A1 | 11/2009 |

OTHER PUBLICATIONS

"Powering Microcontrollers With Scavenged Energy"; Energy Harvesting Solutions, Contributed by Publitek Editors, Aug. 20123 Page Document.
(Continued)

*Primary Examiner* — Santiago Garcia (57) ABSTRACT

A device (10) for converting a movement of a user into a voltage comprises a neck cord (20), a piezoelectric sensor (30) and a printed circuit board (40). The neck cord is coupled to the piezoelectric sensor and provides in use a pulling force that acts on the piezoelectric sensor in a first direction. The printed circuit board is electrically and mechanically coupled to the piezoelectric sensor. The weight of the printed circuit board cause in use a gravity force to act on the piezoelectric sensor in a second direction, which differs from the first direction such that the movement of the user (5) wearing the neck cord causes a change in the shape of the piezoelectric sensor which in response thereto generates the voltage. The voltage may be used as a supply source for an electrical component (41) mounted on the
(Continued)

PCB, or may be used as a wake-up signal for an electrical component such as a processor (41) or an accelerometer.

15 Claims, 9 Drawing Sheets

(51) Int. Cl.
    *A61B 5/00*     (2006.01)
    *H01L 41/113*     (2006.01)
    *H02N 2/18*     (2006.01)
    *A61B 5/11*     (2006.01)

(52) U.S. Cl.
    CPC .......... *A61B 5/747* (2013.01); *H01L 41/1132* (2013.01); *H02N 2/181* (2013.01); *A61B 2562/0219* (2013.01)

(58) Field of Classification Search
    USPC ...................................................... 340/573.1
    See application file for complete search history.

(56) References Cited

U.S. PATENT DOCUMENTS

| | | | |
|---|---|---|---|
| 2004/0094613 A1 | 5/2004 | Shiratori et al. | |
| 2008/0269833 A1* | 10/2008 | Scott | A61N 1/0517 607/44 |
| 2008/0269840 A1* | 10/2008 | Scott | A61N 1/0517 607/60 |
| 2010/0076251 A1* | 3/2010 | Stasz | A61B 5/08 600/28 |
| 2010/0245078 A1 | 9/2010 | Nadkarni et al. | |
| 2011/0132275 A1* | 6/2011 | Huo | A01K 15/021 119/720 |
| 2012/0255349 A1 | 10/2012 | Pop et al. | |
| 2013/0046204 A1* | 2/2013 | Lamego | A61B 5/4884 600/586 |
| 2013/0225954 A1* | 8/2013 | Ludlow | A61H 39/00 600/324 |
| 2014/0180181 A1* | 6/2014 | von Oepen | A61H 23/02 601/47 |
| 2014/0228721 A1* | 8/2014 | Ehrenreich | A61H 23/0245 601/47 |

OTHER PUBLICATIONS

Paradiso: "Systems for Human-Powered Mobile Computing"; DAC'06, Jul. 24-28, 2006, ACM, pp. 645-650.

Shenck et al: "Energy Scavenging With Shoe-Mounted Piezoelectrics"; MIT Media Laboratory, Responsive Environments Group, IEEE, 2001, pp. 30-42.

\* cited by examiner

DEVICE FOR CONVERTING A MOVEMENT OF A USER INTO A VOLTAGE

CROSS-REFERENCE TO PRIOR APPLICATIONS

This application is the U.S. National Phase application under 35 U.S.C. §371 of International Application No. PCT/EP2014/071153, filed on Oct. 2, 2014, which claims the benefit of European Patent Application No. 13188799.4, filed on Oct. 16, 2013. These applications are hereby incorporated by reference in their entirety herein.

TECHNICAL FIELD OF THE INVENTION

The invention relates to a device that converts a movement of a user into a voltage.

BACKGROUND TO THE INVENTION

Devices that convert movement of a user into a voltage may be used for energy harvesting. Energy harvesting is a process by which energy is derived from external sources and converted to electrical energy. An example of an external source is the kinetic energy of a moving person. Piezoelectric materials have the ability to transform mechanical strain energy into electrical charge distribution and are used to convert motion from the human body into electrical energy. For example "Energy Scavenging with Shoe-Mounted Piezoelectrics", by Nathan S. Shenck and Joseph A. Paradiso, MIT Media Laboratory, Responsive Environments Group, http://www.rst2.edu/njheps/resources/energy scavenging.pdf, discloses energy scavenging with shoe mounted piezoelectric materials.

SUMMARY OF THE INVENTION

It is an object of the invention to provide an alternative wearable device that converts the movement of the user wearing the device into a voltage.

The object of the device is achieved with the device according to claim 1. The neck cord allows the user to wear the device around its neck. Movements of the user such as walking will cause a fluctuating pulling force on the piezoelectric sensor. The weight of the printed circuit board (PCB) causes a gravity force to act on the piezoelectric sensor as well. The pulling force and the gravity force act on different portions or locations of the piezoelectric sensor and in different directions causing a fluctuating strain. When external forces mechanically strain the piezoelectric sensor, polarized unit cells in its material shift and align in a regular pattern in the material's crystal lattice. As a result the discrete dipole effects accumulate, developing an electrostatic potential or voltage.

In an embodiment the piezoelectric sensor is shaped as a rectangular element. The rectangular element bends as a result of the pulling and gravity force acting on it in different directions. The pulling forced passed on by the neck cord may be acting on the end portions of the rectangular shaped element whereas the gravity force caused by the mass of the PCB acts on the middle portion. In a further embodiment the pulling force is acting on the middle portion and the gravity force is acting on the end portions of the element. In this embodiment the PCB is coupled to the end portions and the neck cord is coupled to the middle portion of the rectangular element. In both embodiments movement of the user will cause a fluctuating strain on the piezoelectric sensor such that a movement of the user is converted in a voltage.

The piezoelectric sensor may comprise a plurality of rectangular elements each of them being coupled to the neck cord and PCB similar as described in the previous embodiments. Each of the rectangular shaped elements will provide a voltage in response to movements of the user, resulting in an enhanced energy conversion of kinetic energy in electrical energy.

For comfort the device should be relative flat not protrude too much when worn as pendant. Therefore in an embodiment the PCB is positioned in a same plane as the neck cord, which is perpendicular to a bending plane in which the pulling and gravity force cause the rectangular shaped element to bend.

According to a further aspect of the invention there is provided a device for monitoring a user. This device comprises the device for converting a movement of a user into a voltage. The kinetic energy is converted in electrical energy such that the piezoelectric sensor may be used as a supply source for an electrical component. The voltage generated by the piezoelectric sensor may be filtered and buffered, for example with a capacitor, and the filtered and buffered voltage may be used as a voltage supply.

In a further embodiment of the device for monitoring a user the voltage generated by the piezoelectric sensor is used to wake up an electronic component from a standby to an operating state. The device may comprise a battery to supply energy to the electronic component when it is in the operating state. This provides the advantage that energy consumption by the electronic component is limited to the time periods that the user is moving. In the time periods the user is not moving the energy consumption is limited to the standby power. Hence the piezoelectric sensor is not used for energy harvesting but rather as a movement sensor that draws no supply current and awakes the electronic component once movement of the user is detected.

In a further embodiment the device for monitoring a user sends a control signal upon waking up. The control signal indicates that both user and device are active. Absence of the control signal for a predetermined period of time may indicate battery depletion or immobility of the user.

According to a further aspect of the invention there is provided a fall detector comprising a device for monitoring a user. The fall detector includes a movement sensor for measuring the movements of the user and a processor for analyzing and interpreting the measurements from the movement sensor to detect a potential fall of the user. The voltage generated by the piezoelectric sensor is used to wake up the movement sensor and the processor.

In a further embodiment the generated voltage is used to wake up the movement sensor, which on its turn upon measured movements meeting predetermined criteria may wake up the processor. The processor interprets the sensed movements and may cause the transmission of an alarm signal when a possible fall of the user is detected. In an embodiment the movement sensor is an accelerometer.

According to a further aspect of the invention there is provided a system for monitoring a user. The system comprises a device for monitoring a user or a fall detector and a base station for the control signal that may be sent by the monitoring device or fall detector. When no control signal is received for a predetermined period of time the base station sends a warning signal to a caregiver to indicate that the monitoring device or fall detector may need service, or that the user has not been active.

According to a further aspect of the invention there is provided a method of converting a movement of a user into a voltage. The method comprises the steps of causing with a neck cord a pulling force on a piezoelectric sensor and causing with the weight of a printed circuit board a gravity force to act on the piezoelectric sensor. The neck cord passes on the movements of the user to the piezoelectric sensor and the gravity force caused by the weight of the printed circuit board counteracts the pulling force provided by the neck cord causing a strain on the piezoelectric sensor. In use the movement of the user causes a change in the shape of the piezoelectric sensor resulting in energy conversion and the generating of a voltage.

According to a further aspect of the invention there is provide a method of monitoring a user. The method includes in addition to the steps of the method of converting a movement of a user into a voltage the further steps of filtering the generated voltage, comparing the filtered generated voltage with a threshold and switching an electronic component from standby to operating when the generated voltage exceeds the threshold. In this method the generated voltage which results from a detected movement of the user is used as a wake up signal for the electronic component. The electronic component may be used to monitor the activity of the user. This method provides the advantage of a reduced power consumption from a battery supply when the user is not active or has not been active for a period of time.

In an embodiment the method may further include the step of transmitting a control signal when the electronic component has switched from the standby to the operating state after having received the wake up signal. The control signal indicates that the electronic component is active. When the control signal has not been transmitted for a period of time this may indicate that a battery supply has been depleted or that the user has not been active.

According to a further aspect of there is provided a method of detecting a potential fall of a user. The method includes the method of monitoring a user and further includes the steps of monitoring with a movement sensor the movements of the user; and analyzing the measurements from the movement sensor with a processor to detect a potential fall of the user. When the user moves there is a risk of falling. Therefore when a movement of the user is detected with the piezosensor the electronic components such as the movement sensor and the processor wake up to start analyzing the monitored movements.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

Figure 1:
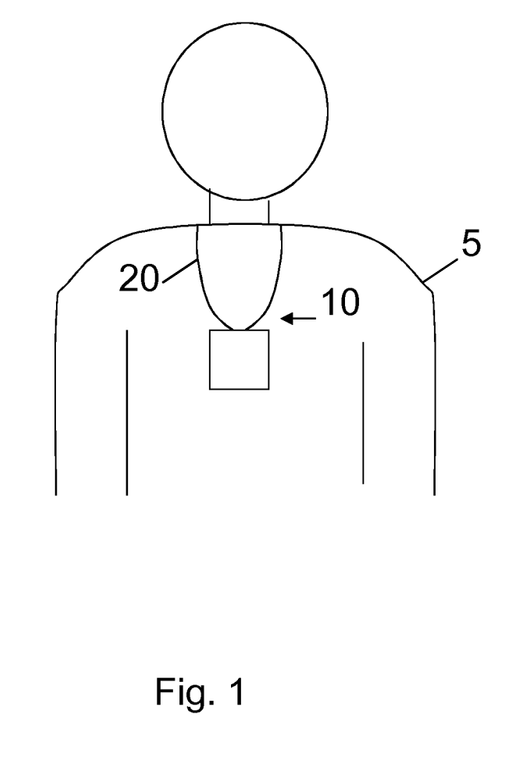
FIG. 1 shows a user wearing a device for monitoring a user.

FIG. 1 shows a user 5 wearing a device 10 for converting a movement of a user into a voltage. The device is worn as a pendent with a neck cord 20 around the neck. When the user is active body movements will cause movements of the device. These movements cause a mechanical strain on a piezoelectric sensor 30 included in the device, see FIG. 2. Due to the mechanical strain the piezoelectric sensor 30 will generate a voltage which is used in the device. The generated voltage may be used to supply (low power) electronic components in the device.

In an embodiment of the device for converting a movement of a user into a voltage the generated voltage is used as a wake up signal for an electronic component. The wake up signal causes the electronic component to switch from a standby or sleep state, in which power consumption is minimal, to an operating state in which the electronic component is active. The electronic component may be for example be a movement sensor such as an accelerometer which measures accelerations in the movements of the user, or a barometric pressure sensor which measures height changes in the movements of the user.

Figure 2:
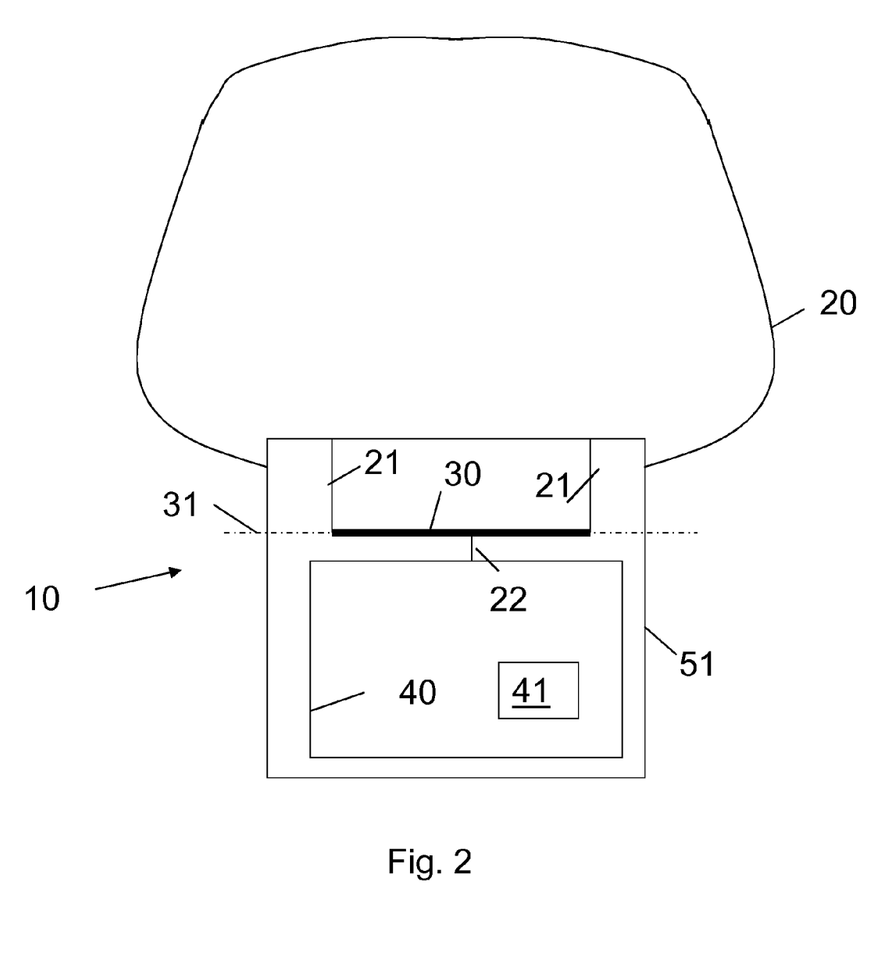
FIGS. 2, 3a, 3b, 4a, 4b, 5a and 5b embodiments of a device for converting a movement of a user into a voltage.

FIG. 2 shows more details of the device 10 for converting a movement of a user into a voltage. The device includes the neck cord 20 which is coupled (or detachably coupled) via the housing 51 and connection elements 21 with the end points of a bendable strip 30 of piezoelectric material such as polyvinylidene difluoride (PVDF) or polyolefin material. The strip may be rectangular shaped but may also have other shapes. A printed circuit board (further referred to as PCB) 40 with one or more electronic components mounted thereon is connected with a further connection element 22 to a middle portion of the strip. The shape of the piezoelectric sensor 30 changes in response to movements of the user: when the user 5 moves (e.g. stands up from a chair) the neck cord 20 will cause an upward pulling force on the strip and due to the downward gravity force caused by the weight of the PCB the strip will bend relative to a plane 31. The PCB carries the electronic component 41 which is electrically coupled to the piezoelectric sensor. When the user 5 wearing the device 10 moves the electronic component 41 receives a voltage. The voltage provided by the piezo electric sensor 30 may need to be rectified, filtered and/or buffered before it is supplied to the electronic component 41 or is used as a supply or wake up signal as will be explained later in more detail with FIGS. 6 and 7.

FIGS. 3a, 3b, 4a, 4b, 5a and 5b show further embodiments of the device 10 for converting a movement of a user into a voltage. The housing and neckcord are not shown in these drawings.

Further when it is stated that the neck cord 20 is coupled to the piezoelectric sensor 30 or strip of piezoelectric material the neck cord may be directly as well as indirectly connected to the piezoelectric sensor or strip of piezoelectric material. With indirectly connected is meant that the neck cord may be connected to the housing which may be connected via a connection element to the piezoelectric sensor or strip of piezoelectric material such that a pulling force of the neck cord is transferred via the housing 51 and the connection element to the piezoelectric sensor or strip of piezoelectric material such as explained in the discussion of FIG. 2.

Figure 3A:
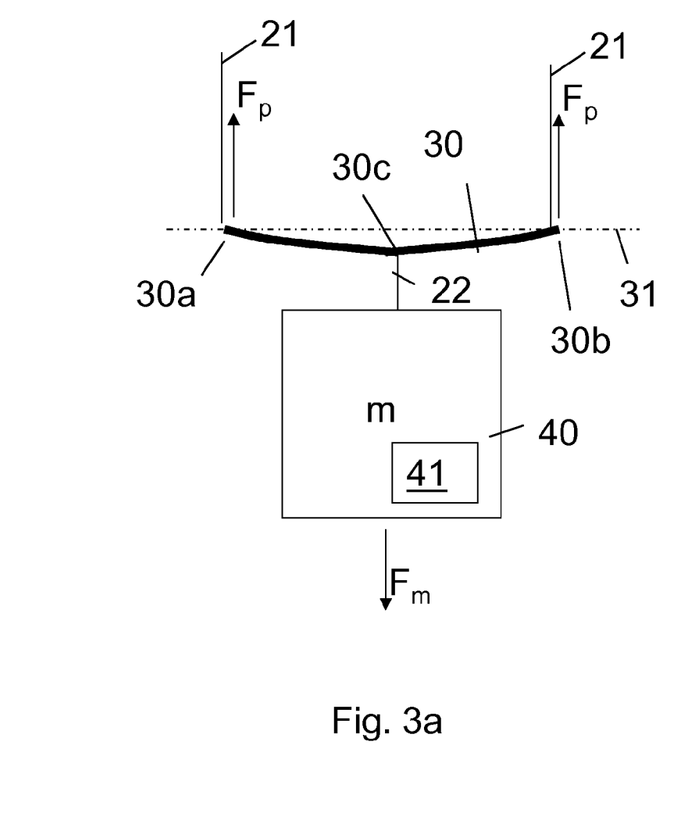
Figure 3B:
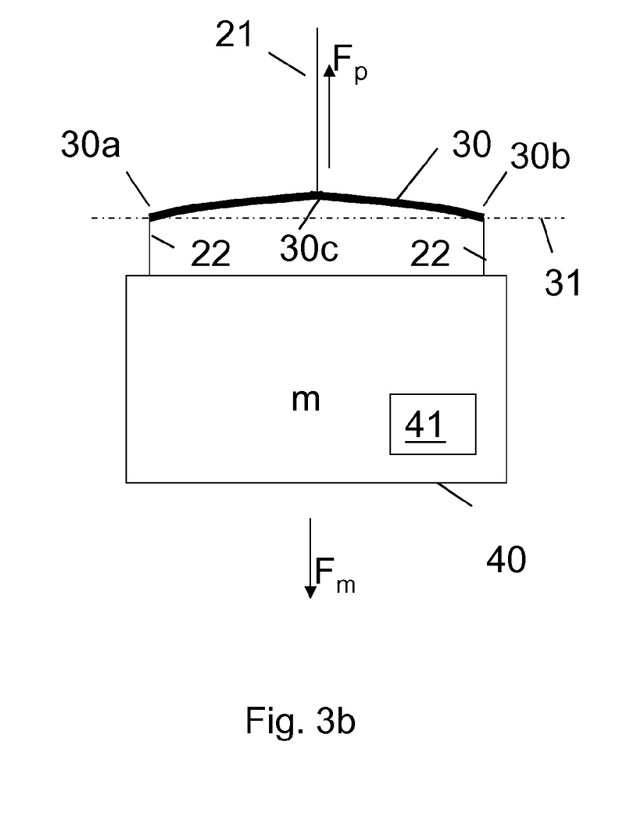

In the embodiments shown in FIGS. 3a and 3b the piezoelectric sensor 30 comprises a piezoelectric rectangular strip 30 having end portions 30a, 30b and a middle portion

30c. The strip is bendable relative to plane 31 which is in parallel with a 'rest position' of the strip. The 'rest position' represents the position of the strip in absence of pulling force Fp and gravity force Fm when there is no mechanical strain acting on it. In use mechanical strain will be caused by the weight of the PCB which is connected via the further connection element 22 to the strip resulting in a gravity force Fm acting on the middle portion 30c, as shown in FIG. 3a, or on the end portions 30a, 30b as shown in FIG. 3b. The pulling and gravity force have different directions. In the embodiment shown in FIGS. 3a and 3b opposite directions. The neck cord provides a pulling force acting on the piezoelectric sensor via the housing and the connection element 21. In the embodiment of FIG. 3a the end portions 30a, 30b are coupled via connection elements 21 to the neck cord and in the embodiment shown in FIG. 3b the middle portion 30c is coupled via connection element 21 to the neck cord. The movements of the user cause a change in the pulling force Fp acting on the piezoelectric sensor while the gravity force resulting from the mass m of the PCB will provide a counter force Fm resulting in change of the mechanical strain. The change in the mechanical strain will cause a change in the bending of the piezoelectric strip relative to its rest position 31 and result in a voltage generation.

Figure 4A:
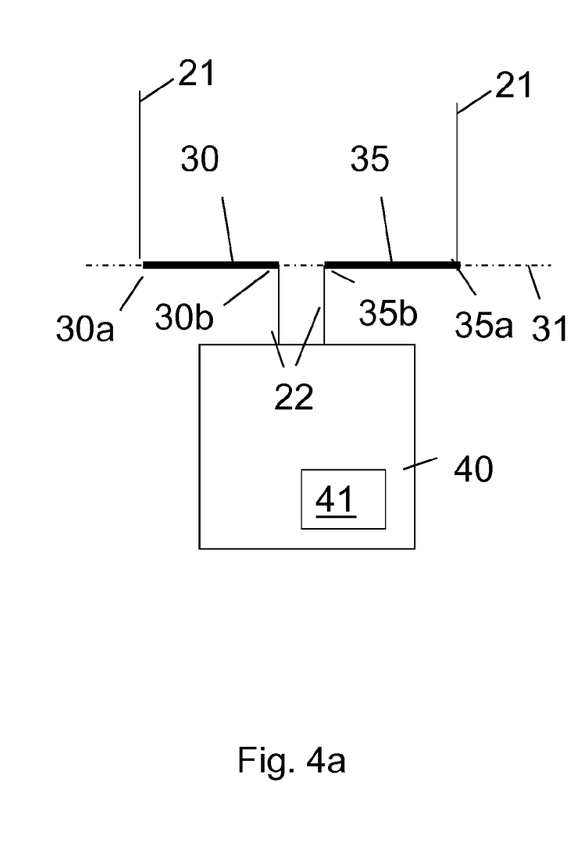
Figure 4B:
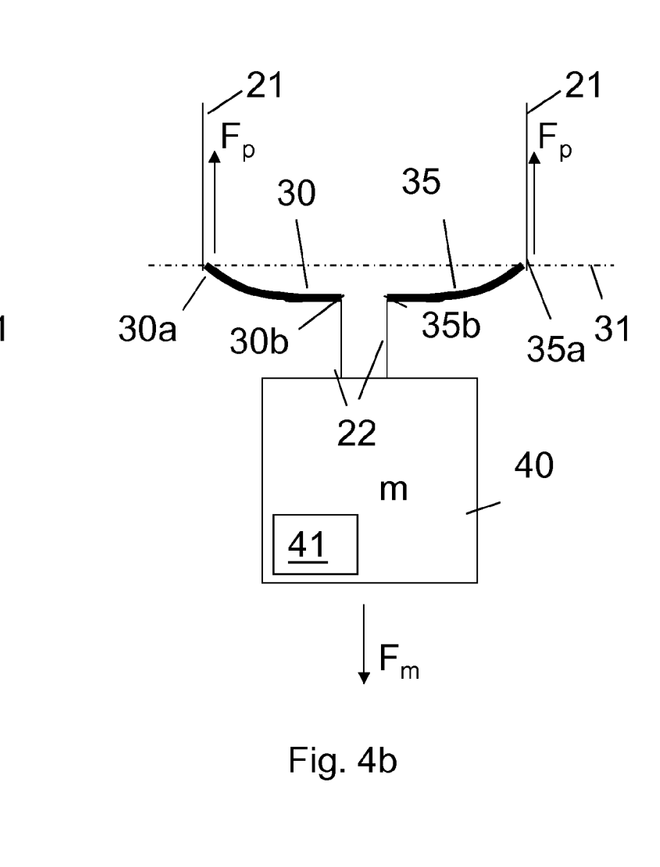

In the embodiments shown in FIGS. 4a and 4b the piezoelectric sensor comprises two piezoelectric rectangular strips 30, 35, each strip having end portions 30a, 30b, 35a, 35b. In both embodiments each strip has an end point 30b, 35b that is coupled with a further connection element 22 to the PCB 40 and the other end point 30a, 35a of each strip is coupled with a connection element 21 to the neck cord 20. The operation of the device for converting a movement of a user into a voltage in these embodiments is similar as discussed with FIGS. 3a and 3b. Due to movement of the user 5 wearing the device 10 the piezoelectric strips 30, 35 will bend relative to their rest position which is illustrated with line 31. Both piezoelectric strips 30, 35 generate a voltage due to the bending and the generated voltage is coupled to the (at least one) electronic component 41 that is mounted on the PCB.

Figure 5A:
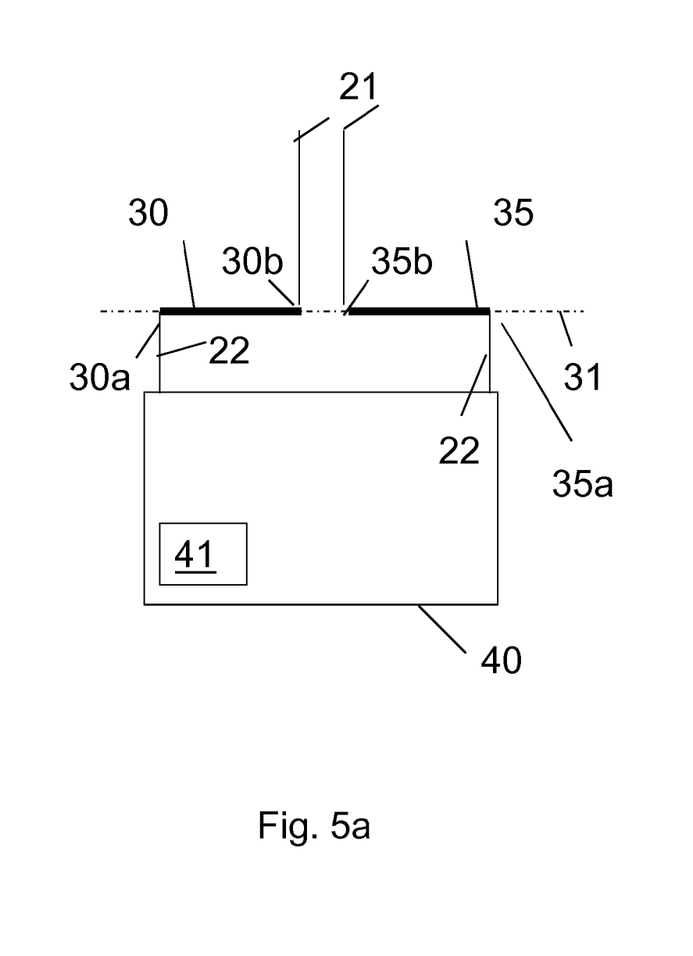
Figure 5B:
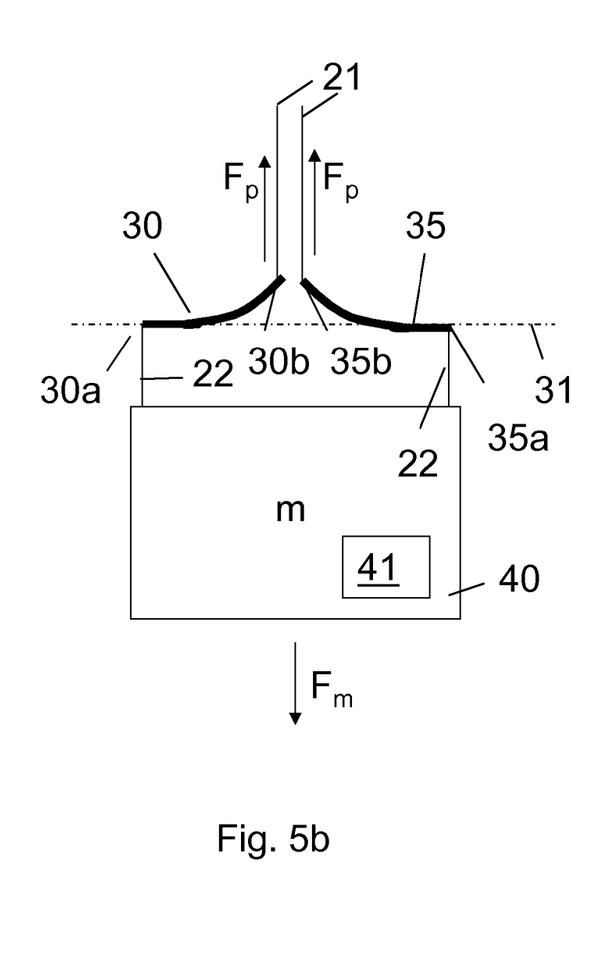

The end points of the strips can be connected in different configurations via connection elements and further connection elements to the PCB and the neck cord. Another configuration is shown in FIGS. 5a and 5b. In the embodiments of FIGS. 5a and 5b the most opposite end points 30a, 35a of the pair of piezoelectric strips are coupled via the further connection elements 22 to the PCB and the end points 30b, 35b of the pair that are most close to each other are coupled via a connection element 21 to the neck cord. The device 10 is worn as a pendant and for comfort preferably should be flat. Therefore in the device the PCB is positioned perpendicular to the bending plane 31 of the strips such that in use when the user stands the PCB is positioned vertical.

Each of the bendable piezoelectric rectangular strips in the embodiments shown in FIGS. 4a, 4b, 5a and 5b may for example be made of PVDF, have a length in the range of 15 mm-20 mm, a width in the range of 0.5 mm-1 mm and a thickness in the range of 40 µm-60 µm. The PCB with the electronic devices mounted thereon may have a weight in the range of 5 to 15 grams.

Figure 6:
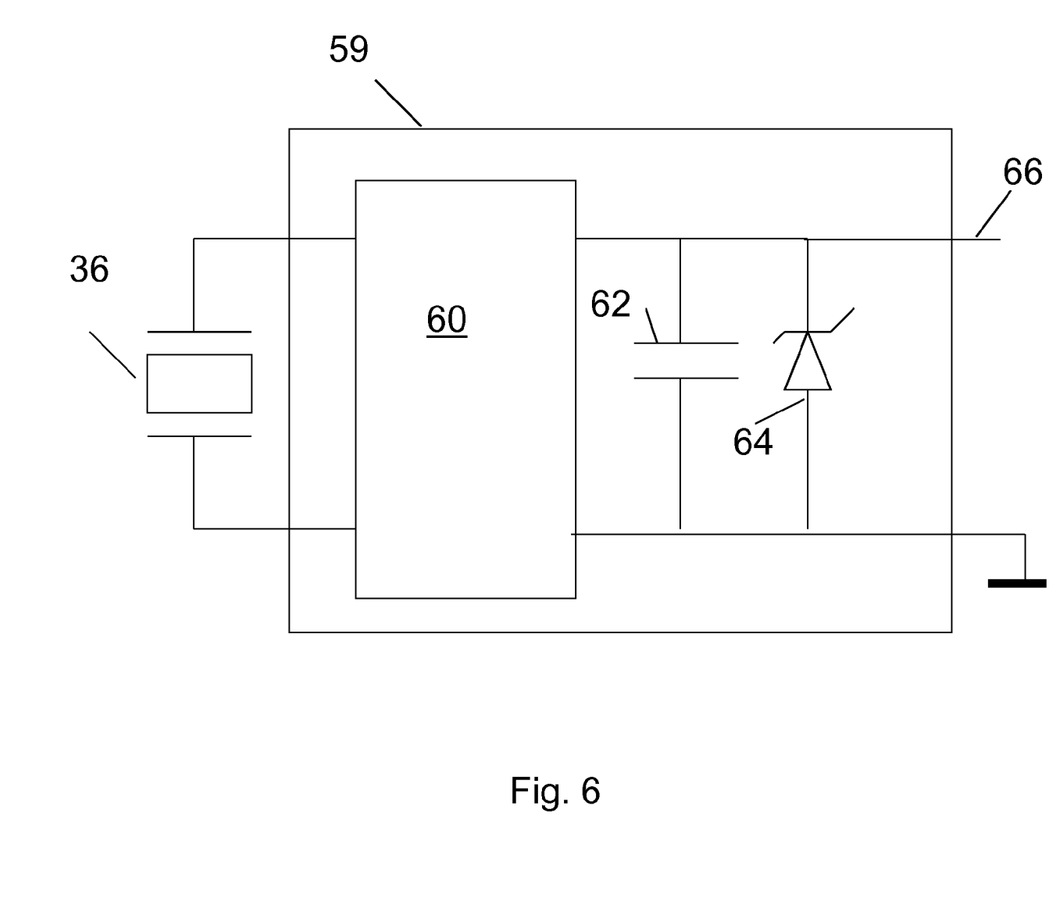
FIG. 6 shows an embodiment of a circuit for use in a device for generating a voltage.

FIG. 6 shows an embodiment of a filter 59 for use in a device for generating a voltage. The filter is electrically coupled with its input to the piezoelectric sensor, which may for example comprise at least one rectangular shaped piezoelectric strip, each strip having a portion coupled to the PCB and another portion via the housing to the neck cord. The user movement induced voltage generated by the piezoelectric sensor 36 is rectified by element 60 which comprises at least one diode. The rectified voltage is filtered and buffered with a capacitor 62 and clamped with clamping element 64, for example a Zener diode, resulting in an output voltage at the output 66 of the circuit. The output voltage 66 may be used as a supply voltage for low power electronic components 41 mounted on the PCB 40. As long as the user moves pulling forces Fp will be exerted on the piezoelectric sensor resulting in the charging of capacitor 62. Hence the movement energy of the user is transduced by the piezoelectric sensor to an electrical energy which is used by the electronic component on the PCB.

A device for converting a movement of a user into a voltage (indicated with in FIGS. 7 and 8 with reference 36) may be included in a device 90 for monitoring a user. Examples of devices for monitoring a user are an activity meter and a fall detector 2, which will be discussed in more detail later when discussing FIG. 8. A monitoring system 100, shown in FIG. 7, may comprise a device 90 for monitoring a user. The device for monitoring a user further comprises an electronic component such as a processor 72 and a sensor 78 (for example an accelerometer). The processor is coupled to a supply source 74, such as a battery, to a transmitter 80 and to the filter 59. The output voltage 66 of the filter is used as a wake up signal 68 for the processor. In response to the wake up signal going from 'low' (indicative for no user movement and thus no generated voltage by the piezoelectric sensor) to 'high' (indicative for user movement resulting voltage generation by the piezoelectric sensor) the processor switches from a standby or sleep state (in which its supply current drawn from the supply source is minimal) to an operating state (in which the processor operates according to its programmed functions). When the user moves the piezoelectric sensor causes the processor to become active. The processor 72 may cause other electronic components such as the sensor 78 to be activated. The measurement data of the sensor is analyzed and interpreted by the processor. The monitoring system 100 further comprises a base station 110. When the processor is activated by the wake up signal 68 it causes the transmitter to send a control signal 82 to the base station. The control signal indicates that the device for monitoring a user, for example a fall detector, is operational. When the control signal is not received for a predetermined period of time the device for monitoring a user may not be functional, for example due to an exhausted battery. The transmitter may further be used to send relevant sensor data and/or an alarm signal to the base station.

Figure 7:
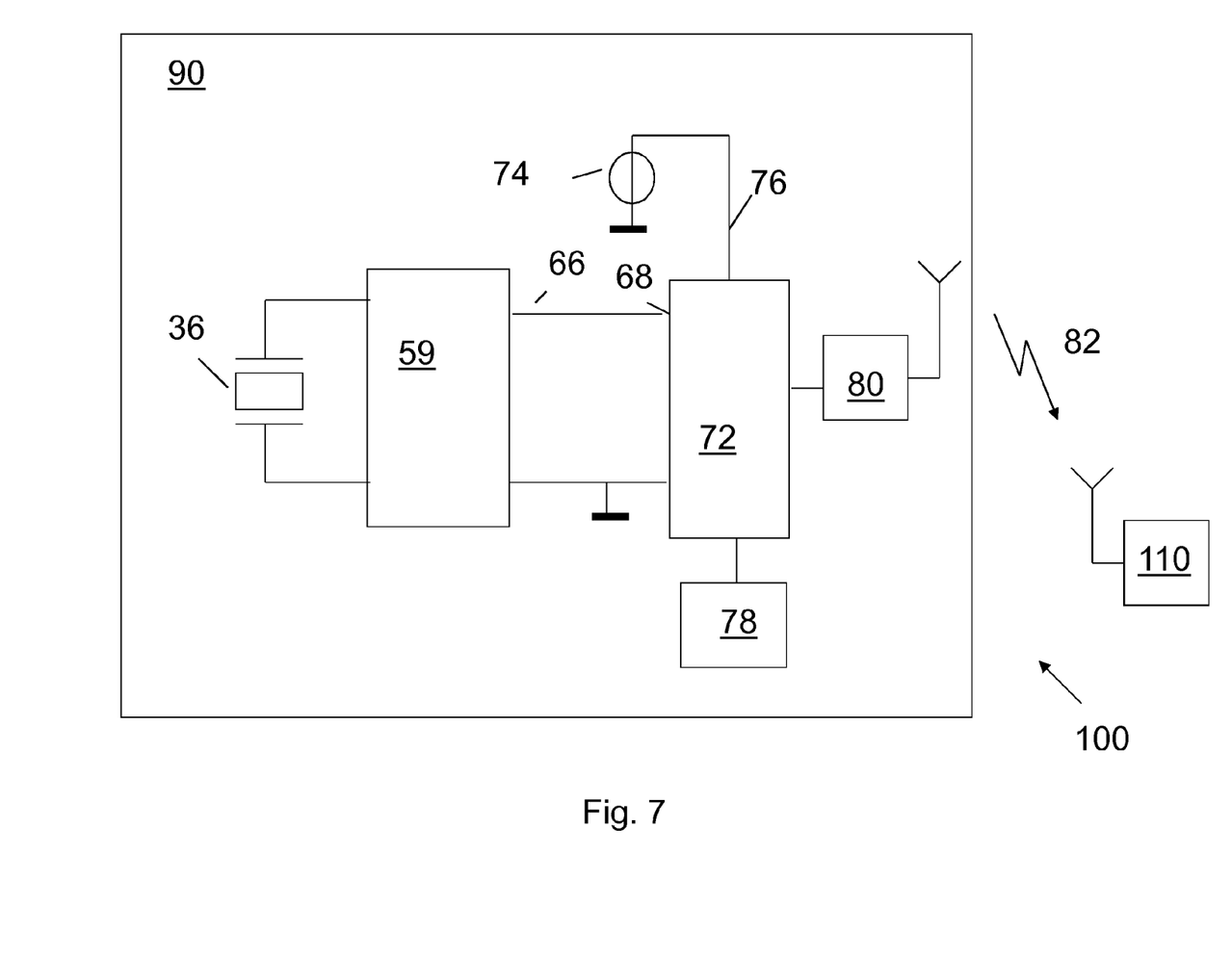
FIG. 7 shows an embodiment of a system according to an embodiment of the invention.

In an embodiment the device for monitoring a user comprises also a receiver which may be combined with the transmitter to form a transceiver 80. The base station may comprise circuitry for enabling communications between the user and a remote call centre (such as the emergency services) via a public switched telephone network and/or a mobile communications network, and/or may provide a connection to the Internet.

Optionally, the device for monitoring a user can include a user interface 16 that provides information to the user and/or allows the user to interact or control the device for monitoring a user. The user interface 16 can comprise user input components, such as buttons, keys, switches, trackballs, touch screens or a microphone; and/or user feedback components, such as a speaker, lights, LEDs, a display or a vibration device (for providing tactile feedback to the user). In some embodiments, the user interface 16 comprises at least a dedicated button for the user to press to request help in an emergency (this button is sometimes known as a personal help button).

In some embodiments, a remotely-located clinician or other healthcare provider can interact with the user via the device 90 for monitoring a user. For example, the clinician or healthcare provider may contact the user via the transceiver circuitry 80 in the device 90 for monitoring a user and advise the user they should perform a fall risk assessment or take some medication.

Figure 8:
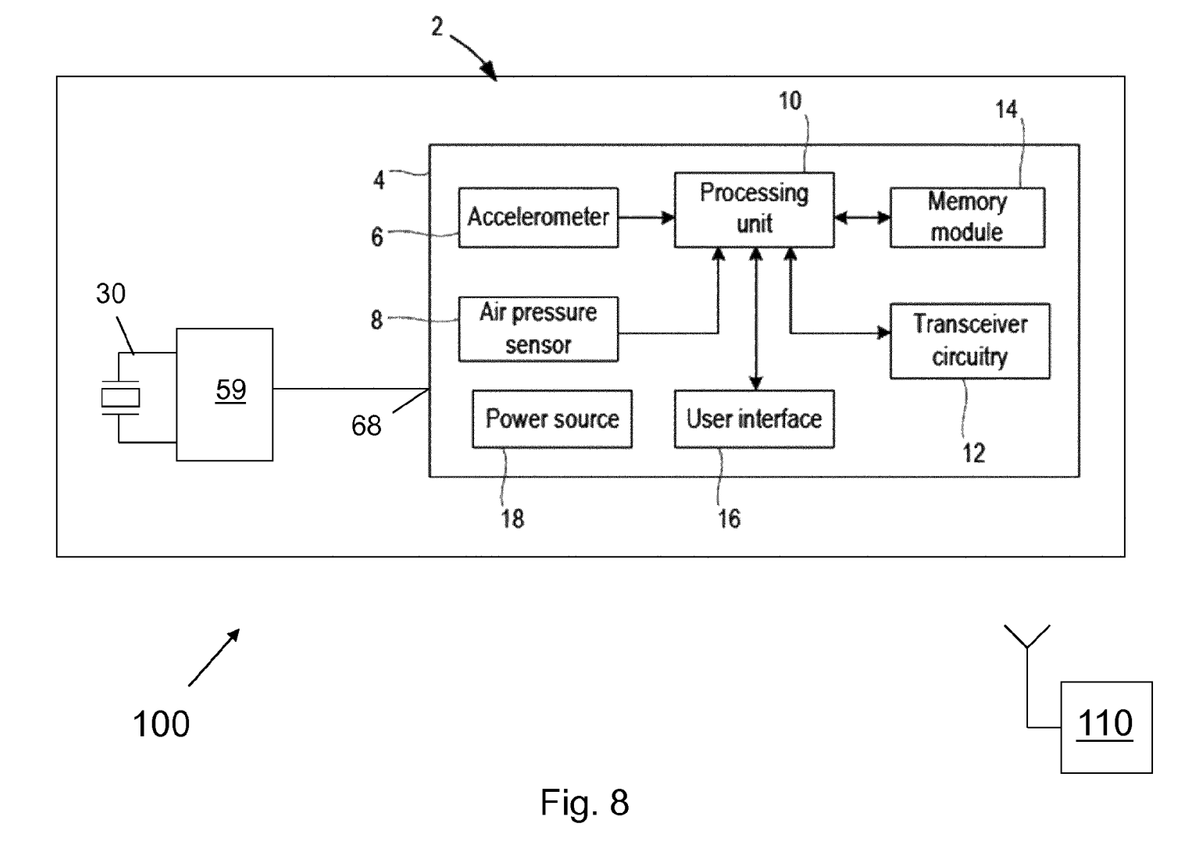
FIG. 8 is a block diagram of an embodiment of a fall detector according to an embodiment of the invention.

In an embodiment the device for monitoring a user is a fall detector. FIG. 8 shows a block diagram of an embodiment of a fall detector 2 according to an embodiment of the invention. In this embodiment of the invention, fall detector 2 is designed to be worn or carried by a user. The fall detector 2 is preferably in the form of a pendant that is worn on a cord or chain around the user's neck. The fall detector 2 comprises the device for generating a voltage (indicated with reference signal 36), a filter 59, and one or more movement sensors for obtaining measurements of the movements of the user. The one or more movement sensors 6, 8 typically includes at least an accelerometer 6 for measuring the accelerations experienced by the user, and in this exemplary embodiment, the fall detector 2 also comprises an air pressure sensor 8 that obtains measurements of air pressure that can be processed to determine the height (altitude) or change in height of the user. The one or more movement sensors 6, 8 are connected to a processing unit 10 which receives a wake up signal from the piezoelectric sensor via filter 59. The processing unit 10 receives measurements from the movement sensors 6, 8, and processes the measurements to determine if the user of the fall detection system 2 has suffered a fall. The processing unit 10 also controls the operation of the fall detector 2. It will be appreciated that the accelerometer 6 measures the accelerations experienced by the fall detector 2, and the processing unit 10 can analyse the accelerations to identify impacts, determine the speed, change in orientation and/or change in position or height of the fall detector 2. The signal from the air pressure sensor can be analysed by the processing unit 10 to determine the height and/or change in height of the fall detector 2. It will be appreciated that although two movement sensors are shown in this embodiment, fall detection systems according to alternative embodiments may comprise only one movement sensor (for example just the accelerometer 6 with the air pressure sensor 8 being omitted). In yet further embodiments, the fall detector 2 can comprise a gyroscope and/or magnetic field sensor(s) in addition or alternatively to the air pressure sensor 8. The fall detector 2 also comprises transmitter or transceiver circuitry 12 that allows the fall detector 2 to transmit an alarm signal to a remote call centre or the emergency services in the event a fall is detected. The transmitter or transceiver circuitry 12 can be configured to communicate with a base station 110 associated with the fall detector 2 (which can then issue an alarm or summon help from a healthcare provider or the emergency services) or via a public telephone network (such as a mobile telecommunications network) to a remote station (for example located in call centre of a healthcare provider). Where the transmitter or transceiver circuitry 12 is configured to communicate with a base station, the circuitry 12 may be configured according to any known wireless technology, for example Wi-Fi, Bluetooth, Zigbee, Near Field Communication (NFC), etc. Where the transmitter or transceiver circuitry 12 is also or alternatively provided to enable communications with a public telephone network, such as a mobile telephone network, the circuitry 12 may be also or alternatively configured for use with any suitable type of second-, third- or fourth-generation communication network, including GSM, WCDMA, LTE, etc. Also, although not shown in FIG. 8, the fall detector 2 may comprise a loudspeaker and/or microphone for enabling a user to communicate with the healthcare provider or the emergency services. The fall detector 2 also comprises a memory module 14 that is connected to the processing unit 10 and that can store measurement data from the movement sensors 6, 8, and/or computer readable code for use by the processing unit 10. It will be appreciated that the memory module 14 may only store the latest measurement data or the measurement data from predefined periods of time. The fall detector 2 also comprises a power source 18, such as a battery that provides power to the components of the fall detector 2. In some implementations of the fall detector 2, the processing and operations according to the invention can be performed by the processing unit 10 in the fall detector 2, with the base unit being provided merely to facilitate communications with the remote call centre/emergency services/Internet. In alternative implementations, the fall detector 2 can communicate the measurements obtained by the movement sensors 6, 8 to the base unit 110, and a processing unit in the base unit can perform the processing and operations using the measurements. This latter embodiment has the advantage that the power consumption of the fall detector 2 can be substantially reduced.

In some implementations the processing unit 10 in the fall detector 2 determines if the user has suffered a fall using a fall detection algorithm by extracting values for a feature or various features that are associated with a fall from the movement sensor measurements. For example, the accelerations and air pressure changes experienced by the fall detector 2 are measured using the accelerometer 6 and air pressure sensor 8, and these measurements are analysed by the processing unit 10 to determine whether the user has suffered a fall.

A fall can be broadly characterised by, for example, a change in altitude of around 0.5 to 1.5 meters (the range may be different depending on the part of the body that the fall detector 2 is to be worn and the height of the user), culminating in a significant impact, followed by a period in which the user does not move very much. Thus, in order to determine if a fall has taken place, the processing unit 10 can process the sensor measurements to extract values for features including one or more of a change in altitude (which can be derived from the measurements from the air pressure sensor 8, but can also or alternatively be derived from the measurements from the accelerometer 6, for example if the air pressure sensor 8 is not present), a maximum activity level (i.e. an impact) around the time that the change in altitude occurs (typically derived from the measurements from the accelerometer 6) and a period in which the user is relatively inactive following the impact (again typically derived from the measurements from the accelerometer 6). A fall by the user can be identified where a subset or all of the above features are identified in the measurements. In other words, a fall may be identified where any one or more of the required height change, impact and inactivity period are detected in the measurements.

Figure 9:
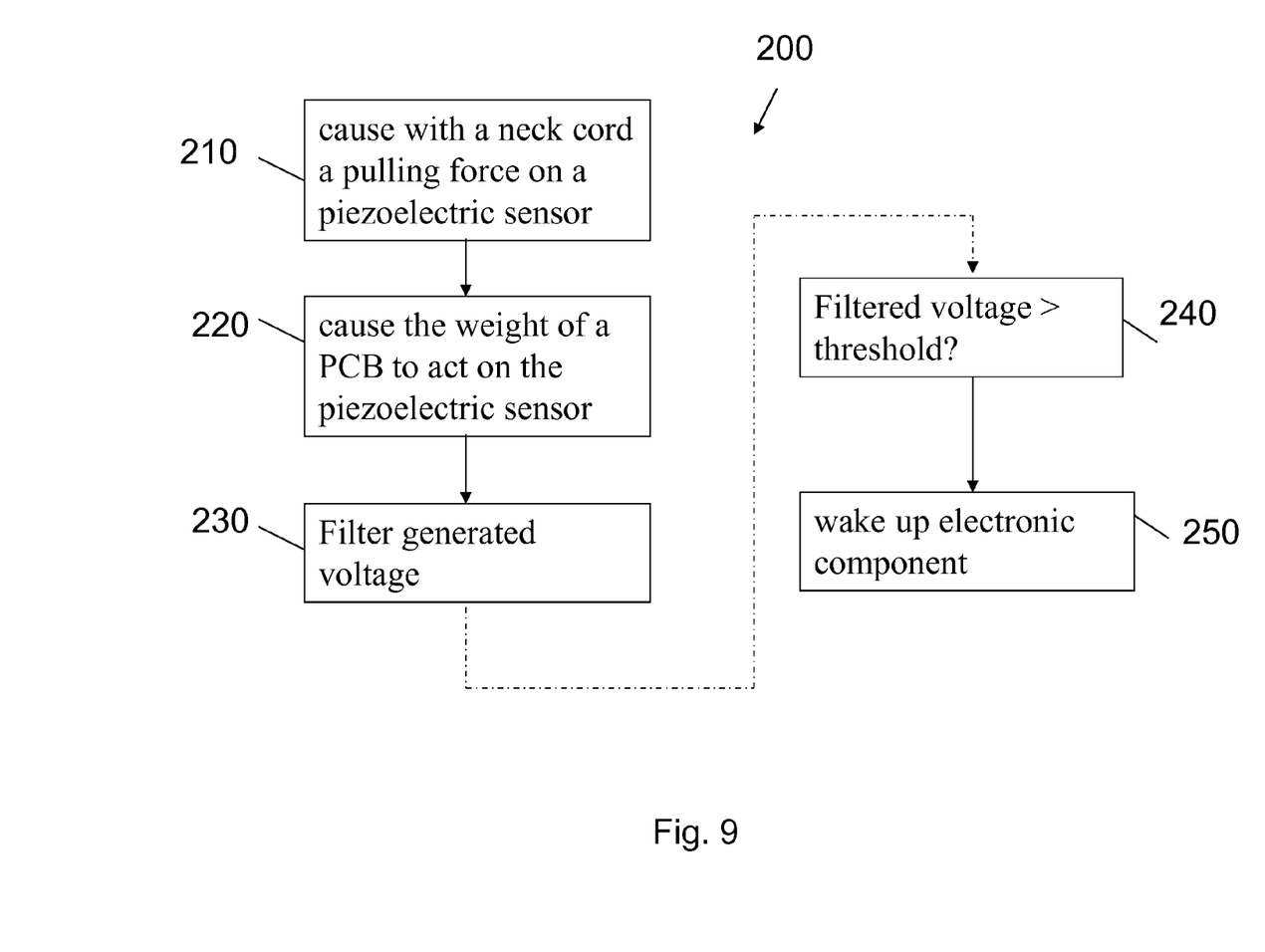
FIG. 9 is a functional flow chart illustrating the operation of an embodiment of the invention.

FIG. 9 is a functional flow chart illustrating the operation of an embodiment of the invention. A method of converting a movement of a user into a voltage comprises the steps 210, 220 of pulling with a neck cord a pulling force on a piezoelectric sensor and causing with the weight of a PCB a gravity force to act on the piezoelectric sensor. When the gravity force acting on the PCB and the pulling force have opposite directions the shape of the piezoelectric sensor will change and a voltage is generated. When the piezoelectric sensor comprises one or more strips, such as discussed above and shown in FIGS. 3a, 3b, 4a, 4b, 5a and 5b, these strips will bend when the user moves, for example when the user stands up from a chair, or when the user walks. The method may comprise a further filtering step 230 in which the generated voltage is filtered and/or buffered. The buffered voltage may be used as a supply source for electronic components mounted on the PCB. The filtered voltage may in a further step 240 be compared with a predetermined threshold voltage. A filtered voltage exceeding the threshold voltage indicates that the user is moving. In a further step 250 an electronic component such as a processor and/or an accelerometer is put from a standby or sleep state into an active or operating state when the filtered output voltage is larger than the predetermined threshold voltage.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A device for converting a movement of a user into a voltage, the device comprising:
a neck cord;
a piezoelectric sensor coupled to the neck cord, wherein the piezoelectric sensor has at least one end point and is bendable relative to a plane including the at least one end point; and
a printed circuit board, coupled to the piezoelectric sensor, wherein the neck cord is arranged to provide in use a pulling force acting on the piezoelectric sensor in a first direction, a weight of the printed circuit board causes a gravity force to act on the piezoelectric sensor in a second direction being different from the first direction such that the movement of the user wearing the neck cord results in a change in the shape of the piezoelectric sensor, the piezoelectric sensor generating the voltage in response to the change in the shape.

2. The device according to claim 1 wherein the piezoelectric sensor is shaped as a rectangular element having two opposite end portions and a middle portion, the element being bendable relative to a plane crossing the end portions, the neck cord being coupled to the end portions of the element, the printed circuit board being mechanically coupled to the middle portion of the element.

3. The device according to claim 1 wherein the piezoelectric sensor is shaped as a rectangular element having two opposite end portions and a middle portion, the element being bendable relative to a plane crossing the end portions, the neck cord being coupled to the middle portion of the element, the printed circuit board being mechanically coupled to the end portions of the element.

4. The device according to claim 1 wherein the piezoelectric sensor comprises two rectangular shaped elements, each element having first and second end portions, each element being bendable relative to a plane crossing its end portions, the neck cord being coupled to the first end portions and the printed circuit board being mechanically coupled to the second end portions.

5. The device according to claim 2 wherein the printed circuit board is positioned perpendicular relative to the plane.

6. A device for monitoring a user comprising the device according to claim 1 wherein the device for monitoring a user further comprises a filter arranged for filtering the generated voltage, the device further comprising an electronic component being arranged to switch from a standby state to an operating state in dependence of the filtered generated voltage exceeding a threshold.

7. The device for monitoring a user according to claim 6 wherein the device is further arranged to transmit a control signal in response to the electronic component switching from the standby state to the operating state.

8. The device for monitoring a user according to claim 6 wherein the electronic component is a processor and/or a movement sensor for measuring the movements of the user.

9. The device for monitoring a user according to claim 6 wherein the electronic component is further arranged to switch from the operating state to the standby state a predetermined time after the voltage is below a further threshold.

10. A fall detector comprising the device for monitoring a user according to claim 6 wherein the electronic component is a movement sensor for measuring the movements of the user, the device further comprising a processor, the processor being arranged to switch from a standby state to an operating state in dependence of a wake up signal received from the movement sensor, the processor being further arranged to process the measurements from the movement sensor to detect a potential fall of the user, the fall detector being further arranged to transmit an alarm signal in response to the processor having detected a possible fall.

11. A system for monitoring a user comprising a base station arranged for receiving the control signal transmitted by the device for monitoring a user according to claim 9, the base station being further arranged to send a warning signal when no control signal has been received for a predetermined time period.

12. A method of converting a movement of a user into a voltage, the method comprising the steps of:
applying a pulling force, via a neck cord, to a piezoelectric sensor in a first direction, wherein the piezoelectric sensor has at least one end point and is bendable relative to a plane including the at least one end point;
applying a second force to the piezoelectric sensor in a second direction via a weight of a printed circuit board coupled to and acting on the piezoelectric sensor in the second direction and the pulling force passed on by the neck cord in the first direction to the piezoelectric sensor cause a change in the shape of the piezoelectric sensor, wherein the piezoelectric sensor generates a voltage corresponding to the change in the shape.

13. The method of monitoring a user comprising the method of converting a movement of a user into a voltage according to claim 12, the method of monitoring a user further comprising the steps of
filtering the generated voltage;
comparing the filtered voltage generated by the piezoelectric sensor with a threshold;

switching an electronic component from standby to operating when the filtered voltage exceeds the threshold.

14. The method of monitoring a user according to claim 13 further comprising the step of:
transmitting a control signal in response to electronic component switching from the standby state to the operating state.

15. The method of detecting a potential fall comprising the method of monitoring a user according to claim 13 and further after the electronic component is switched to operating comprising the steps of:
monitoring with a movement sensor the movements of the user;
processing the measurements from the movement sensor with a processor to detect a potential fall of the user.

* * * * *